US00RE39226E

(19) United States
(12) Reissued Patent
Lappe

(10) Patent Number: US RE39,226 E
(45) Date of Reissued Patent: Aug. 8, 2006

(54) CHANGEABLE MACHINE READABLE ASSAYING INDICIA

(75) Inventor: Murray Lappe, Beverly Hills, CA (US)

(73) Assignee: eScreen, Inc., Overland Park, KS (US)

(21) Appl. No.: 09/852,872

(22) Filed: May 10, 2001

Related U.S. Patent Documents

Reissue of:
(64) Patent No.: 5,902,982
Issued: May 11, 1999
Appl. No.: 09/025,559
Filed: Feb. 18, 1998

U.S. Applications:
(63) Continuation-in-part of application No. 08/832,957, filed on Apr. 4, 1997, now Pat. No. 5,929,422.

(51) Int. Cl.
*G06K 7/10* (2006.01)
*G01J 33/16* (2006.01)

(52) U.S. Cl. ..... 235/375; 235/462.04; 235/494; 422/56

(58) Field of Classification Search ..... 235/462.04, 235/494, 375, 462.16; 422/56, 66; 435/7
See application file for complete search history.

(56) References Cited

U.S. PATENT DOCUMENTS 4,042,329 A * 8/1977 Hochstrasser ..... 422/58
4,059,407 A * 11/1977 Hochstrasser ..... 422/56

* cited by examiner

*Primary Examiner*—Drew A. Dunn
(74) *Attorney, Agent, or Firm*—Hovey Williams LLP

(57) ABSTRACT

A machine readable assaying system including an assay card having a machine readable assaying indicia located upon a surface of the card. At least one analysis element is provided with the assaying indicia, and is capable of monitoring a parameter to detect and optically signal the presence or absence of a desired state. The analysis elements composing, at least in part, an assaying mechanism in the form a pattern of elements, generally additionally including at least one fixed element, and or at least one blank region.

17 Claims, 8 Drawing Sheets

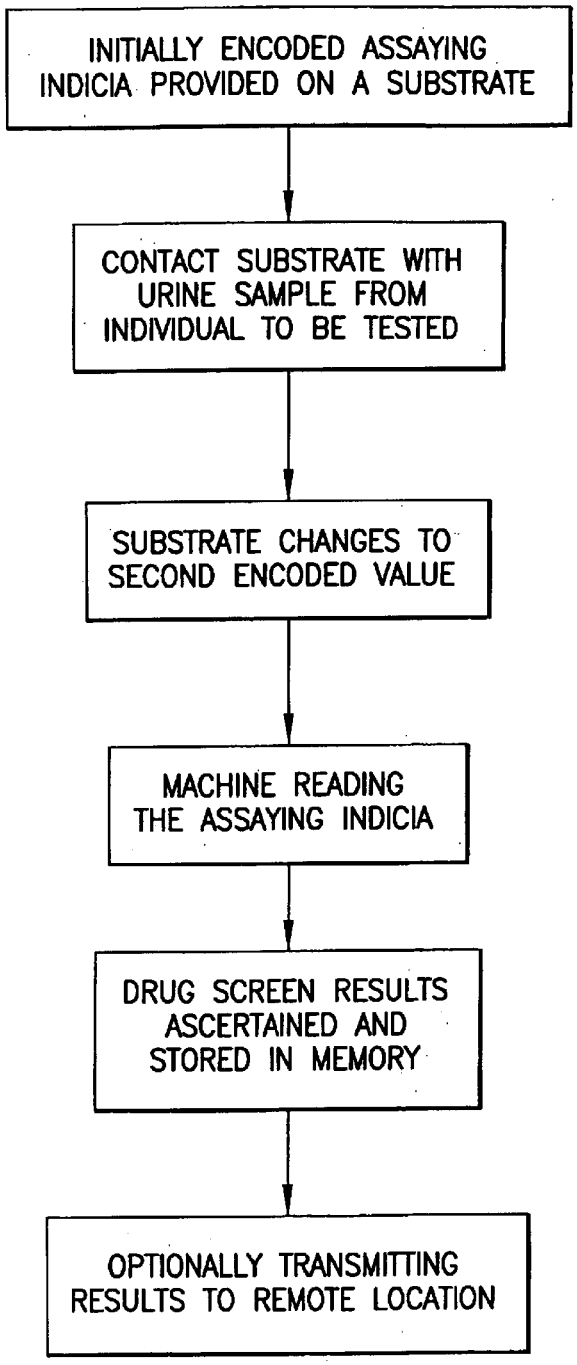
Fig. 7. (AMENDED)

CHANGEABLE MACHINE READABLE ASSAYING INDICIA

Matter enclosed in heavy brackets [ ] appears in the original patent but forms no part of this reissue specification; matter printed in italics indicates the additions made by reissue.

CROSS REFERENCE TO RELATED APPLICATION

The subject matter of this application represents a [continuation] *continuation-in-part* of [copending] application Ser. No. 08/832,957 filed on Apr. 4, 1997, *now U.S. Pat. No. 5,929,422.*

BACKGROUND OF THE INVENTION

1. Field of the Invention

The invention relates to changeable encoded information carrying characters, including bar-code like indicia. More particularly, the present invention relates to embodiments of machine readable, changeable or alterable indicia, wherein the change is related to one or more monitored parameters or variable quantities.

2. Background and Objects of the Invention

The advent of machine readable indicia has been long noted in the art. Such indicia, including for example bar code symbols and other specialized characters, enable encoded data to be read by suitable known apparatus to accurately determine the encoded data. It is this characteristic that has lead to the rapid acceptance of such coding arrangements as defacto standards, especially in inventory intensive establishments that must manage and track a large plurality of items with a significant accuracy. Presently there are a number of industry symbologies and accepted standards available in the art, and a full range of devices to accurately and rapidly read (scan) these indicia.

There is also an on-going need to provide assaying methods, manufactures, and apparatus that provide "assay result indications" which are not subject to errors due to human interpretation, transcription, and or translation. The assay may be required to monitor or determine the levels of parameters and variable quantities. For example, the monitoring of temperature, humidity, saline concentrations (of a fluid), gas concentrations (e.g., the level of exhaust fume gases), chemical residues and associated concentrations, light intensities, magnetic field strengths, radiation exposures, etc. It should also be noted that it is often advantageous to provide an assaying means with a 'memory' capability. For example, it may be desired to monitor if the maximum temperature a package reached in transit, has exceeded a critical level.

Objects of the present invention are, therefore, to provide new and improved assaying arrangements to monitor one or more parameters (or variables) having one or more of the following capabilities, features, advantages and/or characteristics:

- an assaying system that produces machine readable result indications;
- machine readable indicia having changeable or alterable encoded data content;
- assay provided by "elements" composing a machine readable indicia;
- a reliable and expeditious assaying arrangement;
- provides assay means wherein changes and results detected and indicated may be provided as not "human readable", and thus are not subject to interpretation and possible unauthorized dissemination;
- may be employed on-site using a number of relatively low cost "off-the-shelf" components;
- assaying means includes analysis elements that are arranged to provide an optically detectable machine readable change in the assaying indicia; and
- inherently configurable to restrict an assay administrator, or other persons, access to the assay results.

The above indicated advantages, characteristics, objects, and or associated novel features of the present invention, as well as others, will become better understood with a careful review of the description and figures provided herein. Attention is called to the fact, however, that the drawings are illustrative only. Variations are contemplated as being part of the invention, limited only by the scope of the appended claims.

SUMMARY OF THE INVENTION

In a preferred embodiment, the machine readable assaying arrangement includes an assay card formed of a substrate having a surface, and at least one assaying indicia located or disposed upon the surface. Each assaying indicia has an initial encoded value, representing a machine readable source of data, and is capable of detecting and optically signaling the presence of a desired state. Once the desired state of a monitored parameter is detected (i.e., occurs or is present) the assaying indicia forms a second encoded value, different from the initial encoded value. The change of encoded value from the first or initial value to the second value is arranged to be machine readable by a suitable reading apparatus.

The assaying indicia, which represents a machine readable indicia or symbol, is contemplated in a preferred embodiment to include at least one analysis element. Each analysis element is capable of changing from a first state having a first reflectance level to a second state having a second substantially different reflectance level, thereby providing an optical change in reflectance that can be detected and read by the suitable reading apparatus.

If the initial encoded value of the assaying indicia is known, or has been previously read/scanned, a change in the encoded value, as provided by the analysis elements (possible in combination with other elements composing the assaying indicia), can be machine scanned and read to determine if the desired state has or had been attained.

BRIEF DESCRIPTION OF THE DRAWINGS

In the drawings, like elements are assigned like reference numerals. The drawings are not necessarily to scale, with the emphasis instead placed upon the principles of the present invention. The drawings are briefly described as follows:

*FIG. 7 illustrates a method of drug screening an individual in accordance with one embodiment of the invention.*

LIST OF REFERENCE NUMERALS USED IN THE DRAWINGS

10—assay card (p/o assaying arrangement)
20—substrate
20a—surface (of substrate)
32a—assaying indicia (first embodiment)
32b—assaying indicia (second embodiment)
33a—fixed element
33b—blank region
34—analysis element
35—(generalized) elements
38—quality control indication means
42—identification code (pattern)
46—alignment aid
54—assay card reader
54a—scanner unit
54b—decoder
60—assay card reading apparatus
62—controller module
62a—processor
62b—memory unit
62c—interface circuitry
64—user interface module
64a—display
64b—keyboard
64c—audio unit
64d—printer

DETAILED DESCRIPTION OF THE PREFERRED EMBODIMENTS

It is important to establish the definition of several important terms that will be used throughout this disclosure. The term 'encoded value', as applied for assaying purposes, may be assumed to indicate the value provided by reading or interpreting the characters, digits, and or information coded by an assaying indicia of the invention. This value may or may not change or be altered with assaying activities. Further, the encoded value is capable of being machine read and, therefore, may be termed a 'machine readable source of data'.

The definition of a parameter or variable (being monitored or checked for) by the present assaying arrangement may include any quantity or item, including temperature, humidity, pressure, saline concentrations (of a fluid), pH levels, gas concentrations (e.g., the level of exhaust fume gases), chemical residues and associated concentrations, light intensities, magnetic field strengths, radiation exposures, shock forces, as well as others, the term 'desired state' may be assumed to indicate a level or threshold of a parameter has been reached. For example, a desired state may be reached or present if a temperature (being monitored) reaches a critical predefined level, wherein the temperature is the parameter and the desired state is defined as a temperature equal to or above, say, 30 degrees Celsius. Accordingly, for this example, the desired state would be present if the monitored temperature is at 31 degrees Celsius. Finally, 'reflectance level', 'level of reflectance', 'reflectivity' and generally 'reflectance', are assumed to have the meanings known to skilled individuals and refer generally to the measure of the amount of light of a specified wavelength (or series of wavelengths) that is reflected from an illuminated element, region, indicia, and/or surface. Other terms and definitions will be provided as required.

Figure 1:
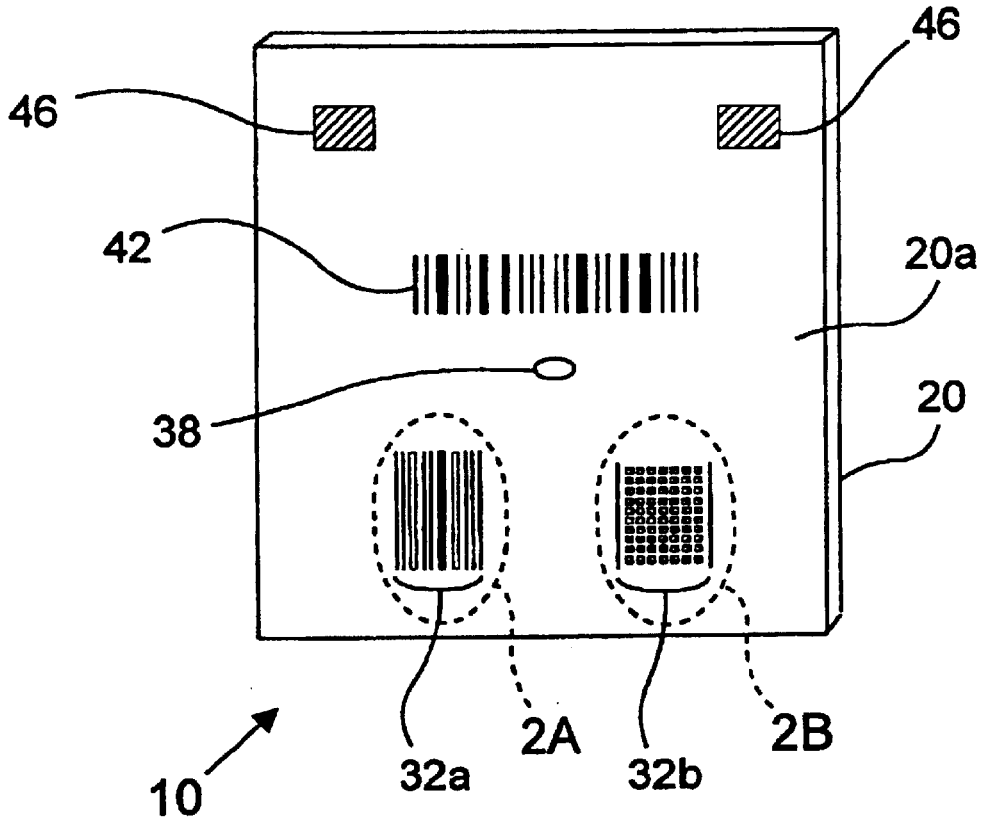
FIG. 1 illustrates a diagrammatic perspective view of an embodiment of an assay card of the machine readable assaying arrangement of the present invention.
Figure 6:
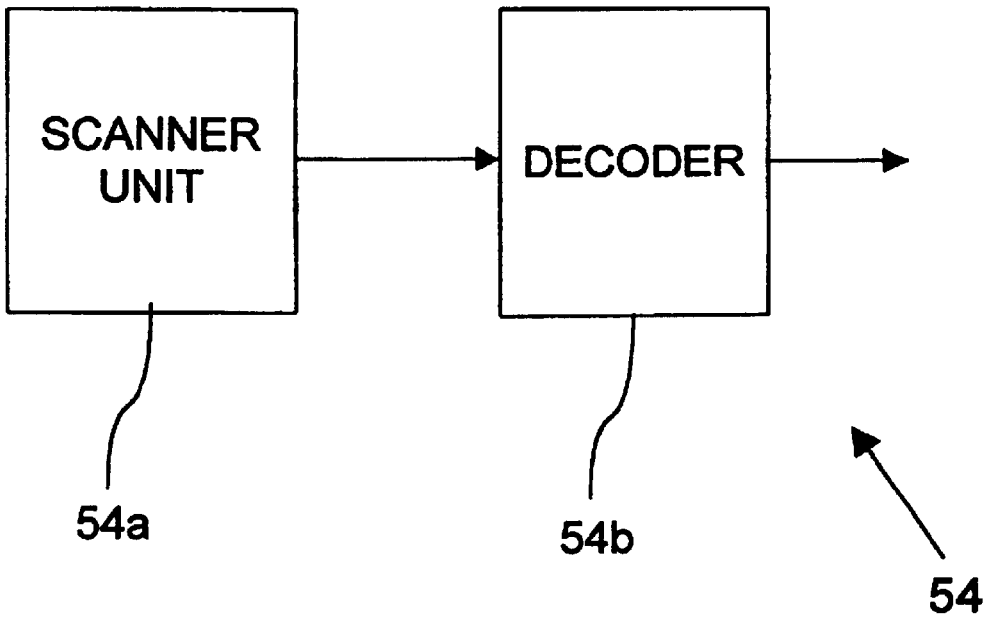
FIG. 6 illustrates an embodiment of the assay card reader of FIG. 5.

FIG. 1 illustrates an assay card 10, which is part of a machine readable assaying arrangement in accordance with the present invention. As can be seen in FIG. 1, the assay card 10 may be provided by a substrate 20 having at least one assaying indicia, such as assaying indicia 32a and 32b, provided upon or impregnated into a surface 20a of the substrate 20. Note: the assaying indicia 32a and 32b of the present invention will be designated, when referred to generally, as an assaying indicia 32a/32b. The assaying indicia 32a/32b, represents a machine readable source of data, and is arranged with an initial encoded value. The initial encoded value may be pre-defined (resulting from the manufacture of the assay card 10) and known, or may be determined or ascertained by employing a suitable reading apparatus. For example, the initial encoded value of the assaying indicia 32a/32b is contemplated to be determinable using a scanner unit, as depicted in FIG. 6. The assaying indicia of the invention are capable of detecting and optically signaling, in a machine readable fashion, the presence of at least one desired state associated with one or more parameters being monitored. It is important to understand that embodiments of the assaying indicia of the present invention, including 32a and 32b, may be arranged to monitor a wide range of parameters and items, as stated and further implied throughout this disclosure.

Figure 2A:
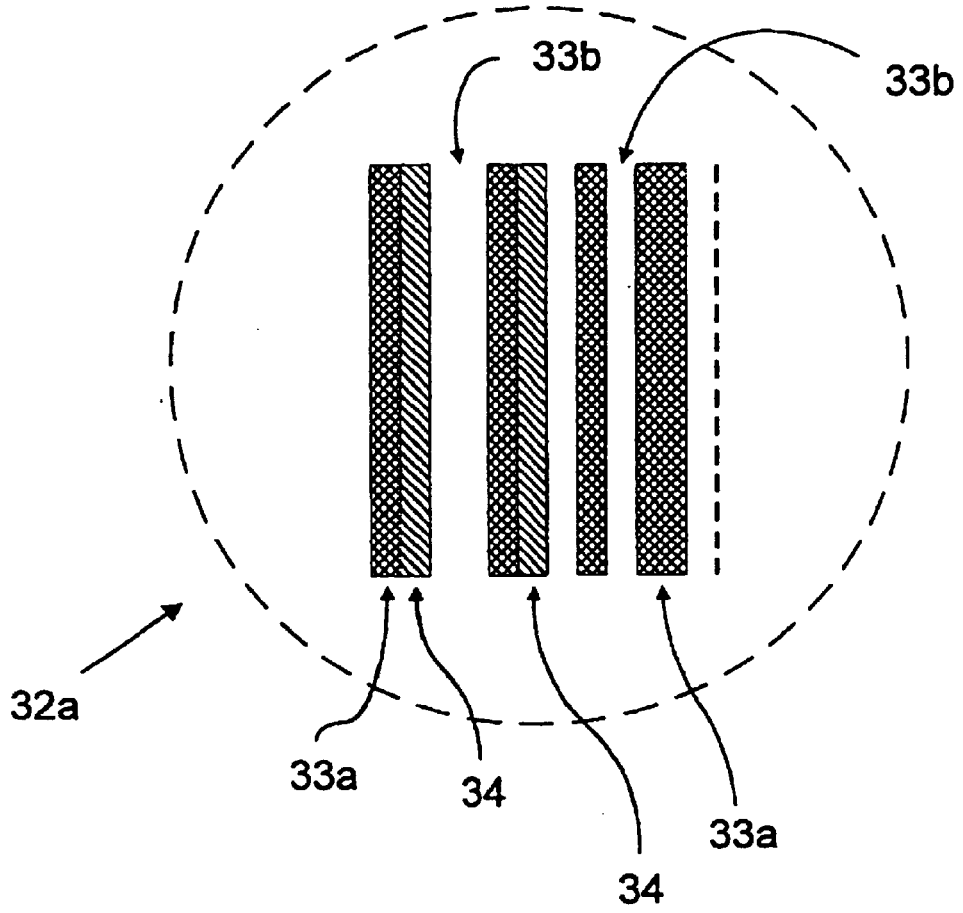
FIG. 2A illustrates an enlarged portion showing an assaying indicia depicted with the embodiment of the assay card in FIG. 1.
Figure 3A:
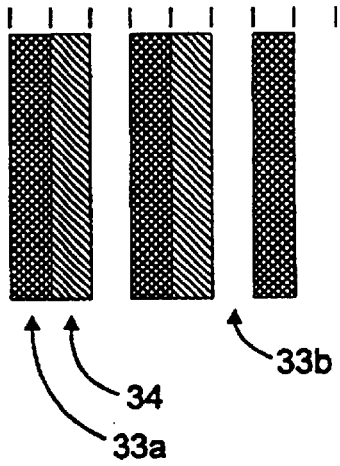
FIGS. 3A and 3B depict possible encoded values that may be provided (as sources of data) by the assaying indicia of FIG. 2A.

In a preferred embodiment the assaying indicia 34a/34b include at least one analysis element 34, as best seen in FIGS. 2A and 3A. Each included analysis element 34, regardless of its shape or composition, may be arranged to monitor one or more parameters to detect and optically signal the presence of a desired state. For example, assume the assaying indicia 32a, as shown in FIG. 2A, is configured to determine if an assay card 10 has been exposed to a strong light source, wherein with such an exposure the indicia changes from an initial encoded value, to the second encoded value. The change in encoded value may be provided by the inclusion of at least one analysis element that is capable of changing from a first state having a first reflectance level (say when not exposed to a strong light source) to a second state having a second substantially different reflectance level (when exposed), thereby providing an optical change in reflectance that can be detected and read by the suitably arranged reading apparatus—as would be well understood by skilled persons.

Referring again to FIG. 1, the assay card 10 may further include quality control indication means 38 provided upon the assay cards 10 to ensure that the analysis elements 34 are functioning properly. As an example, the quality control indication means 38 may be configured to generate a signal if the assay card 10 is improperly stored or if the shelf life thereof has been exceeded, and the assay card 10 should be discarded.

As those skilled in the art will recognize, it is often desirable to have items such as production batch numbers of the assay card 10, the date of manufacture, the specific parameters or quantities the assay card is configured to monitor, etc., provided upon the surface of the assay card. As can be seen in FIG. 1, the assay card 10 may include is an identification code 42, which may be provided as one or more machine readable patterns, for example as bar code indicia, which encodes the required "ID" information. As the identification information, for the most part, will generally be fixed at the time of manufacture, it is contemplated that such information may be provided as both human readable and machine readable, if advantageous. Also seen in FIG. 1 are alignment aids 46 that may be provided to aid in the alignment of the assay card 10 for reading or scanning by a properly arranged reading apparatus. It is important to note that other arrangements of the identification code 42, the quality control indication means 38, and the assaying indicia 32a/32b) are possible and contemplated. For example, skilled persons will appreciate modifications such as including the quality control indication means 38 and the identification code 42 within the elements composing the assaying indicia 32a/32b. Accordingly, such items, when included within the elements composing the assaying indicia may assist in determine the overall "coding" (i.e., the encoded value of the machine readable source of data) provided by said assaying indicia. Still other modifications are possible and contemplated.

Figure 2B:
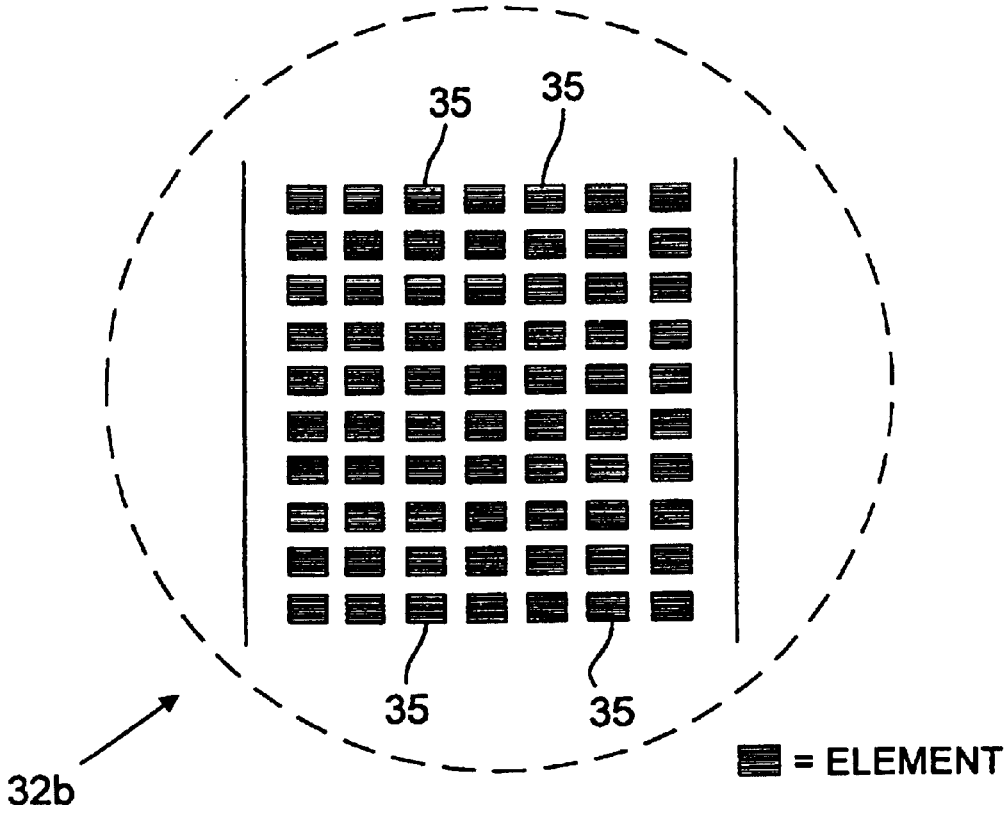
FIG. 2B illustrates another enlarged portion of the assay card of FIG. 1 showing another embodiment of an assaying indicia.

A better understanding of the assaying indicia of the invention, including assaying indicia 32a and 32b, may be gained through FIGS. 2A and 2B. As can be seen in FIG. 2A, the assaying indicia 32a may be comprised of a plurality of elements including fixed elements 33a, blanks regions 33b, and at least one analysis element 34. In a most preferred embodiment of the analysis elements 34, a change will occur if a desired state is present (or achieved), such as, for example, a relative humidity level reaching approximately 50%, where the analysis element 34 will change from a first state having a first reflectance level to a second state having a second substantially different (i.e. machine detectable) reflectance level. Therefore, this substantially different reflectance level change may result in an optically detectable "change", which in accordance with the present invention, may be employable to alter, for example a pattern formed by a plurality of elements, as exemplified in FIGS. 2A through 4C.

Figure 3B:
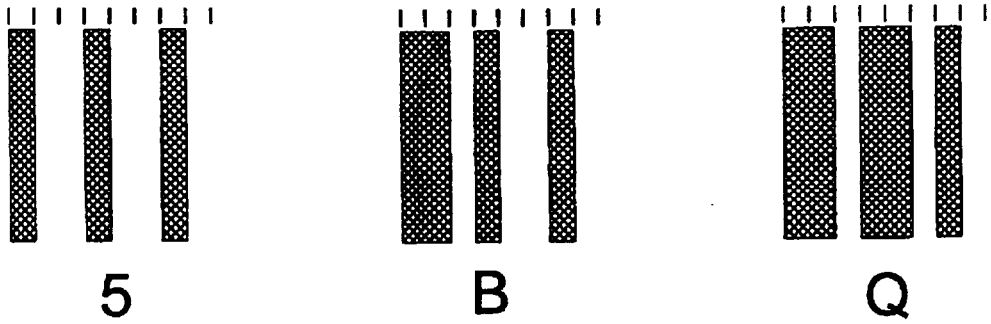

As seen in detail in FIGS. 3A and 3B, a plurality of individual analysis elements 34 are illustrated as an important component of an embodiment of the machine readable assaying indicia 32a, configured in appearance as a bar code indicia. It must be understood that the analysis elements may assume either the first state having a first level of reflectance, or the second state, having the second level of reflectance. As a skilled person will recognize, the first state may provide a high reflectance characteristic (e.g., when being scanned), with the second state exhibiting a low reflectance characteristic. Therefore, an analysis element 34 in the first state may be considered to be the (scanned) equivalent to a 'bar' type element of a bar code symbol. However, clearly the reciprocal arrangement, wherein the first state exhibits a low level of reflectance may be employed. Regardless of the particulars, it must be understood that a desired state is indicated by at least one analysis element 34 essentially changing from a reflective element to a non-reflective element, or visa-versa.

As mentioned earlier, each of the analysis elements 34 may be capable of detecting and optically indicating or signaling the presence of a desired state (which is to be assayed), wherein once the desired state is detected the assaying indicia forms the second encoded value, different from its initial encoded value. Therefore, as can be seen in the arrangement depicted in FIG. 3A, the pattern of analysis elements 34, fixed elements 33a, and blank regions 33b (which may also be termed "bars" and "spaces" by those skilled in the art), when configured to compose the encoded machine readable data source may be provided to encode one or more characters/digits of information or data. Accordingly, by the inclusion of the analysis elements 34 along with the plurality of fixed elements 33a and blank regions 33b, the detection of one or more desired states may cause the overall pattern of fixed elements 33a (bar), analysis elements 34 (bar, spaces), and blank regions 33a (spaces) to vary, and hence, result in the encoded information contained therein being altered.

Referring now to FIG. 3A, there is depicted a sample arrangement of fixed elements 33a, blank regions 33b, and analysis elements 34. As can be seen in FIG. 3B, with two analysis elements 34, a number of possible patterns may be generated or produced resulting in a variety of machine readable and decodeable data patterns. Those skilled in the art will appreciate several considerations that must be addressed when employing standard and or known "symbologies", as well as the symbology exemplified in FIGS. 3A and 3B. First, many commonly employed bar code symbologies include 'check digits' (and the like), as well as items such as guard bars, and start and stop characters. For example, the well known Code-39 symbology, includes a start character on the left side of a bar code and a stop character on the right side. In addition, check or error detecting characters must be considered when one or more analysis elements 34 change from a first state to a second state. This is especially true if it is desirable to employ standard bar code reading equipment with one or more embodiments of the assaying indicia 32a/32b of the invention. Skilled individuals will appreciate these and other considerations that must be addressed to provide for the machine reading of the machine readable sources of data disclosed herein.

It must also be understood that the analysis elements 34 may be arranged to change from the first state to the second state, in the presence of the desired state, and hold the second state, even if the desired state is lost/removed. Alternately, assay card 10 may be arranged with analysis elements 34 that will assume the first state in the presence of the desired state, and assume the second state in the absence of the desired state.

The assay card 10 as provided in the embodiment of FIG. 1 inherently offers an advantage over many known assaying arrangements. Traditionally, assaying means have been configured to visually indicate the positive presence of a desired state. If a "positive" indication was given, it was automatically inferred that the desired state has (or had) occurred. This typically would be clearly discernible to an assay administrator or other person in a position to review the assay results. If for example, an assay test is being conducted for the purposes of drug screening a prospective employee, the individual conducting the test would generally have access to the results of the assay, which may represent a violation of the privacy and civil liberties of the prospective employee. Due to the encoded nature of the source of data of the assaying indicia of the present invention, such privacy concerns may be fully addressed with properly configured assaying indicia 32a/32b provided upon the assay card 10.

Figure 4A:
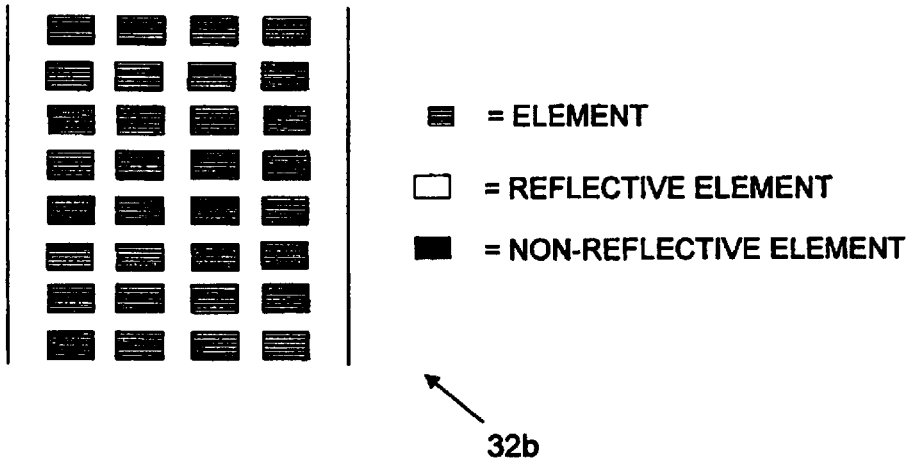
FIGS. 4A, 4B, and 4C depict possible encoded values that may be provided (as sources of data) by the assaying indicia of FIG. 2B.
Figure 4B:
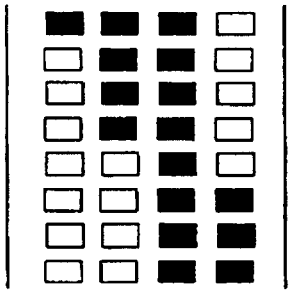
Figure 4C:
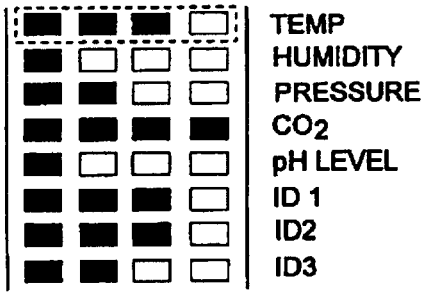

Referring now to FIG. 2B, there is illustrated an alternate embodiment of the assaying indicia of the present invention. Assaying indicia 32b provides a plurality of generalized elements 35, which may be provided by fixed elements 33a, blank regions 33b, and analysis elements 34. As can be clearly seen, the elements 35 may be arranged in a grid or other suitable or advantageous pattern. It should also be noted that the generalized elements 35 may be embodied in other preferred shapes, such as circular or curved bar like versions (not illustrated). The arrangement of FIG. 2B may include a large number of analysis elements 34, with each capable of monitoring a specific parameter. Consider, the exemplary assaying indicia 32b provided in FIG. 4A that consists of thirty-two (32) generalized elements 35. Accordingly, assaying indicia 32b of FIG. 4A may be arranged to monitor 32 individual desired states, if it is assumed that each generalized element 35 is actually provided as an assaying element 34. Such an indicia is depicted in FIG. 4B. Alternately, the arrangement of elements may be provided to provide a "quantized measure" of the level of a parameter being monitored, much as provided by the well known 'bar-type' graphic symbol/element. As shown in FIG. 4B a plurality of parameters, including temperature, humidity, pressure, etc., may be monitored. Consider the TEMP (temperature) elements, which are shown with a dotted line there around. If each element is configured to have a different desired state (i.e., a different temperature threshold value to detect the attaining of the specific desired temp level) say, with each respective element arranged to detect a 5 degree increase in temperature. This simple arrangement provides for the quantized "machine readable" measurement of the present temperature level. Further, is the analysis elements are not sequenced in an ascending or descending order (e.g., they are randomized with respect to their order), the indicated optical assay result (assuming the optical change is in the human visible range) may not be human readable. Accordingly, the analysis elements 34 of FIG. 4B are arranged in a pattern whereby an associated reflective characteristic is formed by a specific plurality of the analysis elements assuming the first reflective state, while a second mutually exclusive plurality of the analysis elements are assuming the second reflective state. The reflectance characteristic may then be read or determined via a suitable reading or interpreting apparatus.

Figure 5:
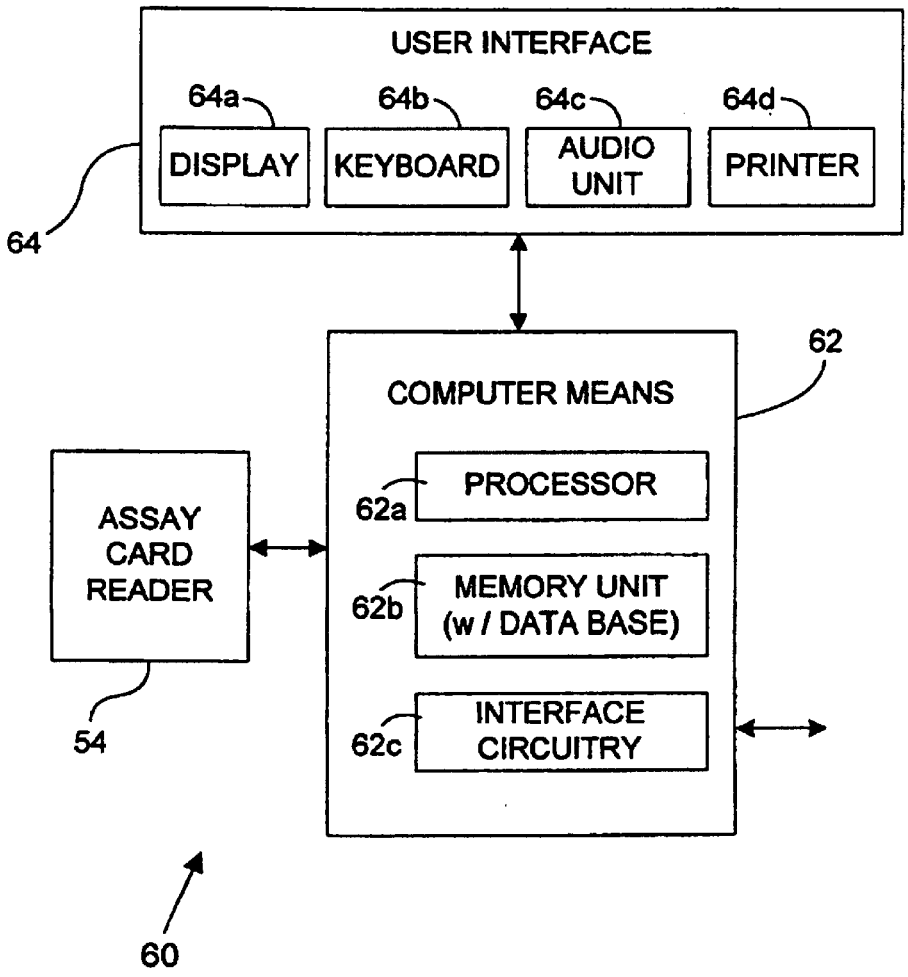
FIG. 5 illustrates a high level system architecture of an embodiment of the assaying arrangement of the present invention.

It should be fully understood that the appearance of the indicia of the present invention, including identification code 42 or assaying indicia 32b, may be provided in many contemplated optical forms. These forms include other patterns that are optically very different in appearance to those illustrated in FIGS. 2A, 3A, and 3B (i.e., the standard bar code type indicia). A key feature, especially considering the arrangement of FIG. 5, is the machine readability of the source of encoded data provided by an employed pattern. Although it may be desirable to utilized standard bar code reading devices, such as scanners and the like, it must be understood that the scope of the present invention should not be limited to just this embodiment of the assaying indicia described herein.

Turning now to FIG. 5, there is provided a high level functional block diagram of a assay card reading apparatus 60. As shown, an assay card reader 54 is included, which is operatively coupled to a suitable computer means 62. The assay card reader 54 is provided to scan and generally "read" and determine the particular patterns, indicia, markings, and the like present upon the assay card 10. As such, the reading of the assay card 10 results in the determining of information, in the form of a plurality of digits or characters, that may possibly be stored by the assay card reading unit 54. The information may then be communicated to the computing means 62, with the determined characters or digits analyzed and applied to determine items, including at least one of the date of manufacture of the assay card, the desired state provided by the assaying indicia, the type/configuration of card, quality control status, etc. Accordingly, all of these items may be provided as "machine readable" indicia and information with a variety of embodiments of the invention.

Those skilled in the art will appreciate the available means to embody the assay card 10 of the invention, and further may provide modifications and alterations, as well as alternate architectures to the disclosed embodiment of the assay card reading apparatus 60 of FIG. 5. Also, although the assay card reader 54 may be provided as shown in FIG. 6, comprised of a scanner unit 54a and decoder 54b (which them selves may include computing modules), other arrangements are certainly possible.

The controller module 62 of FIG. 5 may be embodied as shown by having a processor 62a, a memory unit 62b (providing a suitable application program), and any required interface circuitry 62c. The controller module 62 may be arranged to receive from the assay card reader 54 the information including the one or more (decoded) digits or characters. The information may then be processed for checking and analysis. As can be seen in FIG. 5, a user interface module 64 may be included to enable an individual (such as an assay administrator) to enter information into the assay card reading apparatus 60 and provide information to said individual. The user interface may include known items such as a display 64a, a keyboard 64b, an audio unit 64c, and printer 64d. For example, the administrator's name may be entered into the system, say via keyboard 64b of the user interface module 64. Other user interface items may also be provided (which are not shown in FIG. 5) including pointing devices, a fax transmission modules, touch screen displays, etc. Such devices are known to skilled artisans. It should be noted that the controller module 62 may be provided by known programmable single chip microcomputers and any additional analog/digital circuitry required. Further, it is contemplated that the controller module 62 may be provided (in an alternate embodiment to that shown in FIG. 5) by one or more programmable logic devices (PLDs), or by discrete components including digital MSI and LSI logic functions.

Those skilled in the art will appreciate the number of commercially available (off-the-shelf) devices and components that may be utilized to embody the assay card reader 54 and the assay card reading apparatus 60. They will further recognize alterations and variations are possible, such as including the user interface 64, and or the decoder 54b, as components of a suitably arranged computer means 62. Also, although the scanner unit 54a may in a preferred embodiment be realized by an optical laser scanning device, other suitable devices, such as a CCD imaging device, may be employed. It is also contemplated that the assay card reading apparatus 60 may be realized by a properly configured personal or workstation computer. For example, the ubiquitous Personal Computer (PC) may be arranged with a scanner 54a, required interface and other circuitry, and a suitable custom application program. In such an embodiment, the functionality of the assay card reading apparatus 60 may be essentially provided by the execution of the application program.

The aforementioned configurations of the machine readable assaying system of the present invention, in one contemplated field of use, may utilize these systems on-site at a place of employment for the drug screening of prospective employees. For example, a company that hires skilled and professional employees that are in great demand, may employ the present invention on-site to expedite the hiring process. In a preferred embodiment, a donor individual may be given a collection container (not shown) and provided a private environment where the donor excretes a specimen or volume of urine, into the collection container for analysis. A volume of the urine may then be brought into suitable contact with the assay card 10 (for example, by bathing the assay card 10 with a small amount of urine, inserting the assay card 10 into the urine, etc). The quality control indication means 38 may then be checked, say via scanning and decoding, to verify the integrity of the results indicated by the assaying indicia 32a/32b. Assuming that the assay system is functioning properly, the results of the assay as provided by the reading the assay card 10, may then stored in the memory unit 62b of the controller module 62, and possibly transmitted to a predetermined remote location, such as the centralized laboratory (not shown) for immediate analysis and review.

It is must be understood that the architectural and operational embodiments described herein are exemplary of a plurality possible to provide the same (or equivalent) general features, characteristics, and general system operation. Therefore, while there have been described the currently preferred embodiments of the present invention, those skilled in the art will recognize that other and further modifications may be made without departing from the spirit of the present invention, and it is intended to claim all modifications and variations as fall within the scope of the appended claims.

What is claimed is:

1. A machine readable assaying arrangement, comprising:

(a) an assay card including a substrate having a surface; and (b) at least one assaying indicia provided upon the surface of the assay card and having an initial encoded value representing a machine readable source of data, the assaying indicia capable of detecting and optically signaling the presence of a desired state, wherein once the desired state is detected the assaying indicia forms a second machine readable encoded value, different from the initial encoded value;

(c) each assaying indicia including at least one analysis element, at least one fixed element and at least one blank region therebetween, which collectively form the initial and second encoded values; each analysis element capable of changing from a first state having a first reflectance level to a second state having a second substantially different reflectance level when the desired state is detected, thereby providing an optical change in reflectance producing a change from the initial encoded value to the second encoded value.

2. The machine readable assaying arrangement according to claim 1, wherein a plurality of analysis elements are provided, each capable of monitoring a specific parameter and an associated desired state.

3. The machine readable assaying arrangement according to claim 1, wherein a machine readable source of data is provided by at least one bar code symbol composed of the analysis elements, the fixed elements, and the blank regions.

4. The machine readable assaying arrangement according to claim 3, wherein the analysis elements are arranged in a pattern whereby an associated reflective characteristic is formed by a plurality of the analysis elements assuming the first reflective state, while a second mutually exclusive plurality of the analysis elements are assuming the second reflective state.

5. The machine readable assaying arrangement according to claim 3, wherein the substrate further includes at least one of:

a) quality control indication means capable of determining if the changeable assaying indicia of the assay card are capable of functioning properly;

b) assay card production information; and c) assay card identification information.

6. The machine readable assaying arrangement according to claim 5, wherein quality control indication means, assay card production information, and assay card identification information, are each provided as a machine readable source of data.

7. A machine readable, optically changeable assaying indicia provided upon a substrate for monitoring a present or past desired state of a monitored parameter, the assaying indicia comprising:

(a) at least one fixed element;

(b) at least one blank region; and (c) at least one analysis element, which when considered along with the fixed elements and blank regions, establishes an initial encoded value representing a machine readable source of data;

(d) each analysis element capable of changing from a first state having a first reflectance level to a second state having a second substantially different reflectance level when the desired state is detected, thereby optically signaling the presence of the desired state, wherein once the desired state is detected the assaying indicia forms a second machine readable encoded value, different from the initial encoded value, that is machine readable by a suitable reading apparatus.

8. The machine readable, optically changeable assaying indicia according to claim 7, wherein the analysis elements, fixed elements and the blank regions each have a substantially elongated rectangular shape.

9. The machine readable, optically changeable assaying indicia according to claim 8, wherein the machine readable source of data is provided by at least one bar code symbol comprised, at least in part, by the analysis elements.

10. The machine readable, optically changeable assaying indicia according to claim 8, wherein each respective analysis element, upon the detecting of a respective desired state, changes from the first state to the second state, and maintains the second state, even after the desired state is no longer present and detected.

11. A machine readable assaying system comprising:

(a) an assay card including substrate having a surface;

(b) assaying indicia impregnated upon the surface of the assay card and having an initial machine readable encoded value, the assaying indicia capable of detecting and optically signaling the presence of a desired state, wherein once the desired state is detected the assaying indicia forms a second machine readable encoded value; and (c) an assay card reader arranged to read respective assay cards, and the assaying indicia located thereupon, to determine the encoded value provided by the assaying indicia.

12. The assaying system according to claim 11, wherein the assay card reader includes:

a) an assay card reader having a scanner unit capable of optically scanning and reading the source of data provided by the assaying indicia; and b) computing means for receiving the source of data from the assay card reader and determining assay results.

13. The assaying system according to claim 12, wherein the computing means includes a display means to display to an operator the assay results provided by the reading of assaying indicia.

*14. The assaying system according to claim 11, said indicia responsive to contact with a urine sample as a part of a drug screen.*

*15. A method of drug screening an individual, comprising the steps of:*

*obtaining a urine sample from said individual;*

*providing an assay member supporting a substrate having a surface adapted to be contacted with said urine sample;*

*at least one assaying indicia provided upon said surface and having an initial encoded value, said indicia capable of changing to a second encoded value in response to said contact with said sample,*

*said assaying indicia including at least one analysis element, at least one fixed element, and at least one blank region therebetween and being machine readable only and not human interpretable in the absence of said machine reading, so that others viewing said indicia after said contact with said sample are unable to directly interpret the results of the individual's drug screening assay without said machine reading;*

*machine reading said assaying indicia after said urine contacting step to ascertain the drug screen results; and*

*storing said drug results in electronic memory.*

*16. The method of claim 15, including the step of transmitting said drug screen results to a remote location.*

*17. An assay arrangement designed for drug screening of an individual, said arrangement comprising:*

*a substrate having a surface adapted to be contacted with a urine sample from said individual; and*

*at least one assaying indicia provided upon said surface and having an initial encoded value, said indicia capable of changing to a second encoded value in response to said contact with said sample,*

*said assaying indicia including at least one analysis element, at least one fixed element, and at least one blank region therebetween and being machine readable only and not human interpretable in the absence of said machine reading so that others viewing said indicia after said contact with said sample are unable to directly interpret the results of the individual's drug screening assay without said machine reading.*

* * * * *